United States Patent
Yuan et al.

(10) Patent No.: US 12,201,503 B2
(45) Date of Patent: Jan. 21, 2025

(54) ABSORBENT ARTICLES COMPRISING WETNESS INDICATORS

(71) Applicant: The Procter & Gamble Company, Cincinnati, OH (US)

(72) Inventors: Yi Yuan, Beijing (CN); Paul Thomas Pineda Contreras, Schwalbach am Taunus (DE); Yufei Shan, Beijing (CN); Gueltekin Erdem, Beijing (CN); Yibo Fan, Beijing (CN); Ekaterina Ponomarenko, Koenigstein im Taununs (DE)

(73) Assignee: The Procter & Gamble Company, Cincinnati, OH (US)

( * ) Notice: Subject to any disclaimer, the term of this patent is extended or adjusted under 35 U.S.C. 154(b) by 1482 days.

(21) Appl. No.: 16/671,298

(22) Filed: Nov. 1, 2019

(65) Prior Publication Data
US 2020/0146902 A1    May 14, 2020

Related U.S. Application Data

(63) Continuation of application No. PCT/CN2018/115030, filed on Nov. 12, 2018.

(51) Int. Cl.
*A61F 13/49*    (2006.01)
*A61F 13/42*    (2006.01)
(Continued)

(52) U.S. Cl.
CPC .............. *A61F 13/42* (2013.01); *A61F 13/49* (2013.01); *A61F 2013/15406* (2013.01);
(Continued)

(58) Field of Classification Search
CPC ................. A61F 13/42; A61F 13/53708; A61F 13/53713; A61F 13/53756; A61F 13/5376;
(Continued)

(56) References Cited

U.S. PATENT DOCUMENTS 5,458,592 A  * 10/1995  Abuto .................. A61F 13/531
                                                      604/378
8,853,487 B2   10/2014  Takeuchi et al.
(Continued)

FOREIGN PATENT DOCUMENTS

CN        102753127 A    10/2012
CN        104582653 B     4/2015
(Continued)

OTHER PUBLICATIONS

PCT International Search Report dated Jan. 27, 2019.
International Search Report and Written Opinion; Application Ser. No. PCT/CN2018/115030; dated Feb. 26, 2021; 8 pages.

*Primary Examiner* — Catharine L Anderson
(74) *Attorney, Agent, or Firm* — Daniel S. Albrecht; Christian M. Best (57) ABSTRACT

A nonwoven web for an absorbent article is provided. The absorbent article comprises the nonwoven web as a core wrap. A method for producing the absorbent article is also provided. The nonwoven web comprises a first nonwoven layer comprising filament fibers, a second nonwoven layer comprising filaments fibers, a third nonwoven layer comprising staple fibers disposed between the first and second nonwoven layers. A total basis weight of the first and second nonwoven layers is not less than about 10 gsm. The third nonwoven layer has a basis weight no greater than about 4 gsm. The nonwoven web comprises pores, wherein greater than about 80% of the pores have a pore size equal to or smaller than about 40 μm, and wherein less than about 10% of the pores have a pore size equal to or greater than about 45 μm.

10 Claims, 5 Drawing Sheets

(51) Int. Cl.
  *A61F 13/15* (2006.01)
  *A61F 13/511* (2006.01)
  *A61F 13/512* (2006.01)
  *A61F 13/531* (2006.01)

(52) U.S. Cl.
  CPC ............... *A61F 2013/15495* (2013.01); *A61F 2013/15552* (2013.01); *A61F 2013/15959* (2013.01); *A61F 2013/15967* (2013.01); *A61F 2013/422* (2013.01); *A61F 2013/51178* (2013.01); *A61F 2013/5127* (2013.01); *A61F 2013/5315* (2013.01)

(58) Field of Classification Search
  CPC .. A61F 2013/15406; A61F 2013/15495; A61F 2013/15552; A61F 2013/5315; A61F 2013/530868; A61F 2013/530897; A61F 2013/53721; A61F 2013/53726; A61F 2013/5373
  See application file for complete search history.

(56) References Cited

U.S. PATENT DOCUMENTS

| | | | |
|---|---|---|---|
| 2005/0054999 A1* | 3/2005 | Morman | A61F 13/537 604/367 |
| 2006/0135932 A1 | 6/2006 | Abuto et al. | |
| 2008/0312617 A1* | 12/2008 | Hundorf | A61F 13/15658 156/60 |
| 2011/0064928 A1 | 3/2011 | Bonneh | |
| 2011/0137274 A1 | 6/2011 | Klofta et al. | |
| 2011/0196327 A1 | 8/2011 | Chhabra et al. | |
| 2012/0111627 A1 | 5/2012 | Kato et al. | |
| 2014/0276503 A1 | 9/2014 | Sheldon et al. | |
| 2015/0173967 A1 | 6/2015 | Kreuzer et al. | |
| 2017/0224544 A1* | 8/2017 | Decker | B29C 48/0021 |
| 2018/0360671 A1 | 12/2018 | Joseph | |

FOREIGN PATENT DOCUMENTS

| | | |
|---|---|---|
| CN | 2206261741 U | 6/2017 |
| CN | 107374831 A | 11/2017 |

\* cited by examiner

ABSORBENT ARTICLES COMPRISING WETNESS INDICATORS

CROSS REFERENCE TO RELATED APPLICATION

This application is a continuation of, and claims priority under 35 U.S.C. § 120 to, Patent Application No. PCT/CN2018/115030, filed on Nov. 12, 2018, the entire disclosure of which is hereby incorporated by reference herein.

FIELD OF THE INVENTION

The invention is directed at absorbent articles for personal hygiene that are worn in the crotch region of the wearer, for example baby diapers, training pants and adult incontinence products. The articles comprise a wetness indicator.

BACKGROUND OF THE INVENTION

Disposable absorbent articles such as diapers and adult incontinence products are well known in the art. Such disposable articles are designed to absorb and contain body exudates, in particular large quantity of urine. These absorbent articles comprise several layers, for example a topsheet, a backsheet and in-between an absorbent core, among other layers.

Many disposable absorbent articles comprise a wetness indicator signaling the occurrence of the wetness event. Wetness indicators may comprise a colorant adapted to change in appearance, i.e., appear, disappear, change color, etc., upon contact with liquids such as, urine, runny bowel movements, menses, etc., in the article. The color change of the wetness indicator should occur as quickly as possible after the wetness event.

Meanwhile, softness of the absorbent article is one of prioritized requirements. Majority of absorbent cores comprise an absorbent material at least partially wrapped with a core wrap. One type of commonly used absorbent materials is a blend of comminuted wood pulp (so-called "air-felt") with superabsorbent polymers ("SAP"). Another type of cores having SAP without cellulose fibers (so called "airfelt-free" cores) has been more recently proposed which can reduce a total basis weight of absorbent articles comprising the same. One concern associated with absorbent core comprising SAP is the migration and penetration of SAP to a core warp which causes a loss of SAP. Several approaches to prevent SAP leakage from absorbent core were suggested. WO2001/39707A discloses an intermediate absorbent structure comprising SAP in the form of particles, an upper layer and a lower layer that is impervious to the penetration of SAP, and has a mean pore size in the range 5-25 μm wherein at least 70% of the pores have a diameter in the range 5-15 μm, a tensile strength in the machine direction of at least 20 N/5 cm and a tensile strength in the cross direction of at least 10 N/5 cm. U.S. Pat. No. 5,458,592 discloses a meltblown core wrap having a plurality pores with a mean flow pore size less than about 30 μm and no more than 5% of the pores have a pore size greater than 50 μm.

In some absorbent articles, especially in absorbent articles having a lower basis weight and/or a high percentage of SAP, in particular a particle form of SAP, a negative touch feeling known as "graininess" coming from the SAP particles needs to be improved. A grainy feeling may be improved by increasing a basis weight of a soft nonwoven at most outside of the article which the consumers can directly touch. However, it brings increase in production cost as a soft nonwoven is relatively expensive and a basis weight increase causes a material cost increase. In addition, users' directly contact of the outermost soft nonwoven may bring the negative of "fuzz" at the outer nonwoven.

Some absorbent articles have a wetness indicator which allows the caregiver to observe the timing of the change of the absorbent article without taking the wearer's absorbent article off. It is desirable a wetness indicator can react quickly after a fluid insult's, communicating at an early stage to the caregiver that the diaper has been wetted.

Based on the foregoing, there is a need for an absorbent article providing an improved softness without compromising perception of a wetness indicator color change.

There is also a need for an absorbent article providing an improved softness while keeping the cost of manufacturing as low as possible.

SUMMARY OF THE INVENTION

The present invention relates to a nonwoven web for an absorbent article, the nonwoven web comprising a first layer comprising spunbond nonwoven, a second layer comprising spunbond nonwoven, and a third layer comprising meltblown nonwoven disposed between the first and second layers, wherein a total basis weight of the first and second layers is not less than about 10 gsm, wherein the third layer has a basis weight no greater than about 4 gsm. The nonwoven web comprises pores, and greater than about 80% of the pores has a pore size equal to or smaller than about 40 μm, and less than about 10% of the pores has a pore size equal to or greater than about 45 μm.

The present invention also relates to an absorbent article comprising a liquid pervious topsheet, a liquid impervious backsheet comprising a wetness indicator, an absorbent core disposed between the topsheet and the backsheet, the absorbent core comprising an absorbent material and a core wrap comprising a nonwoven web according to the present invention.

The present invention also relates to processes for manufacturing absorbent articles of the present invention.

BRIEF DESCRIPTION OF THE DRAWINGS

In the drawings, like numerals or other designations designate like features throughout the views.

DETAILED DESCRIPTION OF THE INVENTION

Various non-limiting forms of the present disclosure will now be described to provide an overall understanding of the principles of the structure, function, manufacture, and use of an absorbent article comprising fastening members having unique shape. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the term "absorbent article" refers to disposable devices such as infant, child, or adult diapers, adult incontinence products, training pants, sanitary napkins and the like which are placed against or in proximity to a body of a wearer to absorb and contain the various fluids (urine, menses, and/or runny BM) or bodily exudates (generally solid BM) discharged from the body. Typically, these absorbent articles comprise a topsheet, backsheet, an absorbent core, leg cuffs, optionally an acquisition system and/or a distribution system (which may be comprised of one or several layers), and typically other components, with the absorbent core normally placed at least partially between the backsheet and the acquisition and/or distribution system or between the topsheet and the backsheet. The absorbent articles comprising a fastening member of the present invention will be further illustrated in the below description and in the Figures in the form of one or more components of taped diaper. Nothing in this description should be, however, considered limiting the scope of the claims. As such the present disclosure applies to any suitable form of absorbent articles (e.g., diapers, training pants, adult incontinence products, sanitary napkins).

The term "air permeability" is defined by the Air Permeability Test set forth below. Air permeability is set forth in $m^3/m^2/minute$ (m/min).

"Elastic," and "elastomeric" mean the ability of a material to stretch by at least 25% without rupture or breakage at a given load, and upon release of the load the elastic material or component exhibits at least 80% recovery (i.e., has less than 20% set).

The term "filament(s)" or "filament fiber(s)" as used herein means an elongate particulate having a length greater than or equal to 5.08 cm and/or greater than or equal to 7.62 cm and/or greater than or equal to 10.16 cm and/or greater than or equal to 15.24 cm.

The term "fiber" refers to any type of artificial fiber, filament, or fibril, whether continuous or discontinuous, produced through a spinning process, a meltblowing process, a melt fibrillation or film fibrillation process, or an electrospinning production process, or any other suitable process.

The term "film" means a sheet-like material wherein the length and width of the material far exceed the thickness of the material (e.g., 10×, 50×, or even 1000× or more), and it does not comprise individually distinguishable fibers. Thus, "film" does not include a nonwoven material. Films are typically liquid impermeable but may be configured to be breathable by known technologies such as by being perforated or apertured.

The term "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

The term "lateral" (and forms thereof), with respect to a line lying in a plane substantially occupied by an absorbent article fastening member laid flat and horizontally, viewed from above, relates to a direction substantially perpendicular to a longitudinal axis of the absorbent article.

The term "longitudinal" and "length" (and forms thereof), with respect to a line lying in a plane substantially occupied by an absorbent article fastening member laid flat and horizontally, viewed from above, relates to a direction approximately aligned with the wearer's spine when the article would be normally worn, with the wearer in a standing or extended reclining position.

The term "nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Comprise," "comprising," and "comprises" are open ended terms, each specifies the presence of what follows, e.g., a component, but does not preclude the presence of other features, e.g., elements, steps, components known in the art, or disclosed herein.

The term "staple fiber(s)" as used herein means an elongate particulate having a length less than 5.08 cm and/or less than 3.81 cm and/or less than 2.54 cm.

The terms "web" or "web of material" refer to a sheet-like structure such as a nonwoven or a film.

Absorbent Article

Figure 1:
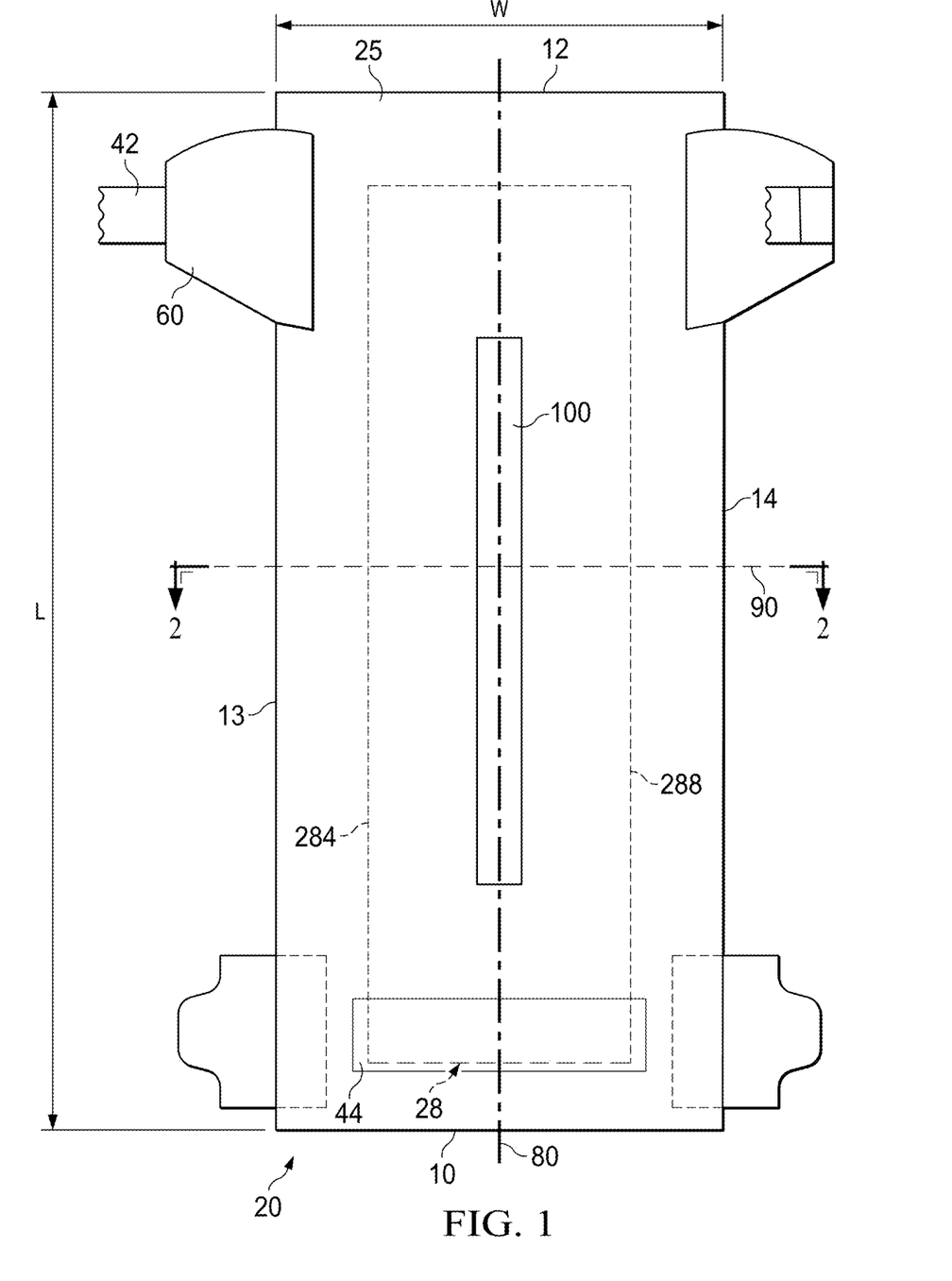
FIG. 1 is schematic plan view of an exemplary absorbent article according to the present invention.

Absorbent articles will now be generally discussed and further illustrated in the form of a baby diaper 1 as exemplarily represented in FIG. 1. FIG. 1 is a perspective view of the exemplary diaper 1 in a flattened-out configuration with the taped ends opened and the garment-facing side turned up. An article that is presented to the user closed such as a training pant may also be represented flattened out by cutting it along its side waists. The absorbent article will typically have a front edge 10, a back edge 12 and the longitudinally-extending lateral side edges 13, 14. The front edge 10 forms the edge of the front waist and the back edge 12 of the back waist, which together when worn by the wearer form the opening for the waist of the wearer. The lateral edges 13, 14 can each form one of the leg openings. The article has a longitudinal direction and a transverse direction defined by the longitudinal axis 80 and lateral axis 90 respectively. The taped back ends 42 attached on the front of the diaper to such as a landing zone 44.

The longitudinal axis 80 extends through the middle of the front and back edges 10, 12 of the article, and thus virtually divides the article in symmetrical left side and right side. The article has a length L along this longitudinal axis between the front and back edges 10, 12 of the article. The lateral axis 90 extends perpendicularly to the longitudinal axis. The article has a width W along this lateral axis between the lateral edges 13, 14 of the article.

The absorbent articles of the invention comprise at least a wetness indicator 100 visible through the garment-facing area of the article. When the wearer urinates in the absorbent article, the channels distribute the fluid longitudinally along their length. The wetness indicators which are at least partially superposed with the channels can thus react quicker to a first liquid insult, providing a very early warning to the caregiver that urination has occurred. The wetness indicator 100 may typically be a color-change composition.

Figure 2:
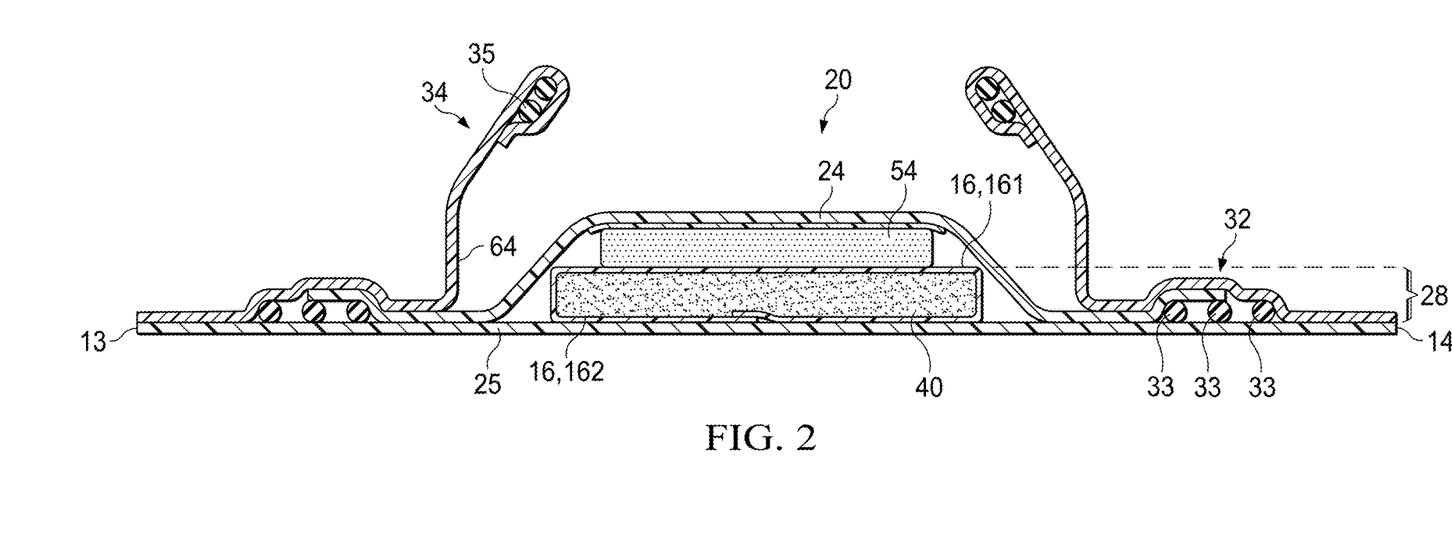
FIG. 2 is a lateral cross-section of the absorbent article of FIG. 1.

Other layers of the absorbent article are better illustrated in FIG. 2, which shows in cross-section in addition to the liquid permeable topsheet 24 and the liquid impermeable backsheet 25, an absorbent core 28 between the topsheet 24 and the backsheet 25. An optional acquisition and/or distribution layer 54 is represented on the article of FIG. 2 together with other typical diaper components. Typical acquisition and/or distribution layers 54 may not comprise SAP as this may slow the acquisition and distribution of the fluid, but an additional layer may also comprise SAP if some fluid retention properties are wished. The prior art discloses many type of acquisition and/or distribution layers that may be used, see for example WO2000/59430 (Daley), WO95/10996 (Richards), U.S. Pat. No. 5,700,254 (McDowall), WO02/067809 (Graef).

The absorbent article may typically comprise a pair of partially upstanding barrier leg cuffs 34 having elastic elements 35 and elasticized gasketing cuffs 32 substantially planar with the chassis. Both types of cuffs are typically joined to the chassis of the absorbent article typically via bonding to the topsheet and/or backsheet. All or a portion of the barrier leg and/or gasketing cuffs may be treated with a lotion. The absorbent article may also comprise other typical components, which are not represented, such as a back-elastic waist feature, a front elastic waist feature, transverse barrier cuff(s), a lotion application, etc.

Absorbent Core

As used herein, the term "absorbent core" refers to a component used or intended to be used in an absorbent article and which comprises an absorbent material and a core wrap. As used herein, the term "absorbent core" does not include the topsheet, the backsheet and (if present) any acquisition-distribution layer or multilayer system, which is not integral part of the absorbent core. The absorbent core is typically the component of an absorbent article that has the most absorbent capacity of all the components of the absorbent article. The terms "absorbent core" and "core" are herein used interchangeably. The absorbent core may comprise one or more channels.

The absorbent material comprise a liquid-absorbent material commonly used in disposable absorbent articles such as comminuted wood pulp, which is generally referred to as airfelt or fluff Examples of other suitable liquid-absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (herein abbreviated as "SAP"), absorbent gelling materials, or any other known absorbent material or combinations of materials.

The absorbent material in the absorbent core can be any type. It can be an airfelt core comprising wood cellulose fibers such as pulp fibers mixed with SAP, or an airfelt-free core free of such cellulose fibers. Airfelt cores typically comprises from 40% to 80% of SAP. For absorbent cores comprising a relatively high proportion of SAP at least partially enclosed within the core wrap, the SAP content may represent in particular at least 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent core may comprise an absorbent material comprising at least 80%, at least 90%, at least 95%, or at least 99% by weight of absorbent material. The term "superabsorbent polymer" refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example.

An absorbent core in the present invention comprises a core wrap which at least partially wrap the absorbent material. According to the present invention, the core wrap, as described herein, may be used at least on one side of the absorbent core to cover at least a portion, or substantially all, or all of the respective side of the absorbent material.

Core wraps may comprise any known type of nonwoven comprising natural fibers, synthetic fibers or combination thereof. Examples of suitable synthetic fibers which may comprise all or part of the core wrap substrates of the present invention include but are not limited, to nylon (polyamide), acrylic (polyacrylonitrile), aramid (aromatic polyamide), polyolefin (polyethylene and polypropylene), polyester, butadiene-styrene block copolymers, natural rubber, latex, spandex (polyurethane) and combinations thereof.

Nonwoven used for the core wrap may be characterized in that it does not show large holes, enabling it to effectively retain SAP during production of the absorbent article and during use.

An absorbent core has an upper, body-facing side and a lower, garment-facing side. The absorbent material may either be sandwiched between two separately provided sheets of core wrap materials, or wrapped by folding one sheet of core wrap material, for example in a C-fold, to envelope the absorbent material. When the core wrap material is intended to cover the body facing side of the absorbent core it may be desirable for material to be hydrophilic. In certain embodiments, nonwoven may be rendered hydrophilic by means known in the art. The core wrap may be used to cover only the garment-facing side of the absorbent material. In certain embodiments it may be preferred that the core wrap described below covers the body-facing side of the absorbent material.

The absorbent core may comprise a relatively high amount of SAP of more than 80% or 85% or 90% or 95% by weight of the absorbent core. Furthermore, the absorbent core may comprise a hot melt adhesive, as will be described in more detail below. In an embodiment, the absorbent core comprises the super polymer material, the hot melt adhesive and the core wrap, wherein the amounts of these materials add up to present 99% or 100% by weight of the absorbent core. Absorbent articles having absorbent cores with a high percentage of SAP, while it may be typically thin and conformable, may cause users to feel a negative touch feeling known as "graininess". In view of the above-mentioned reasons core wraps which can be able to provide reducing graininess feeling is wanted.

In embodiments where a core wrap comprises two separately provided sheets of material, at least one of the sheets can comprise a nonwoven web of the present application. In embodiments where a core wrap comprises a single sheet of core wrap material, the edges of the folded sheet may be sealed together to enclose the absorbent material. Sealing may be facilitated at least along the longitudinal edges of the absorbent core. Alternatively, the core wrap may be sealed completely along all edges.

Referring to FIG. 2-5, the core wrap 16 may comprise a top layer 161 generally forming the top side, i.e., wearer-facing side of the core and a bottom layer 162 generally forming the bottom side, i.e., the garment-facing side, of the core wrap 16. The top and bottom layers, 161, 162, may be formed by a single substrate, or may be formed two separate substrates which may be the same or different material. They may be the same substrate coated with the same hydrophilicity boosting composition, the different substrates coated with the same hydrophilicity boosting composition or different substrates coated with different hydrophilicity boosting composition, etc. The top layer 161 may be hydrophilically treated. The bottom layer 162 may be inherently hydrophobic but air-permeable.

The core wrap 16 can be any of known core wrap constructions. For example, the core wrap is formed of a single substrate wrapped around the absorbent material with one single seal. The top and bottom layers can be attached or sealed by gluing or otherwise to form at least one C-wrap seal along each of the longitudinally-extending side edges 284, 286 of the core.

Figure 3:
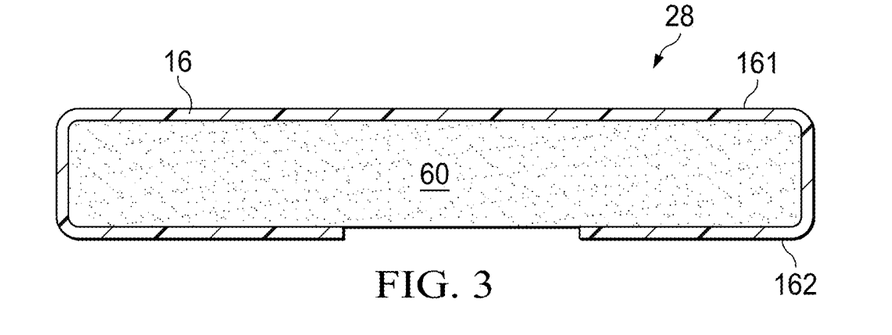
FIG. 3 is a partial sectional view along 2-2 of one alternative embodiment of the absorbent core of the absorbent article of FIG. 1.
Figure 4:
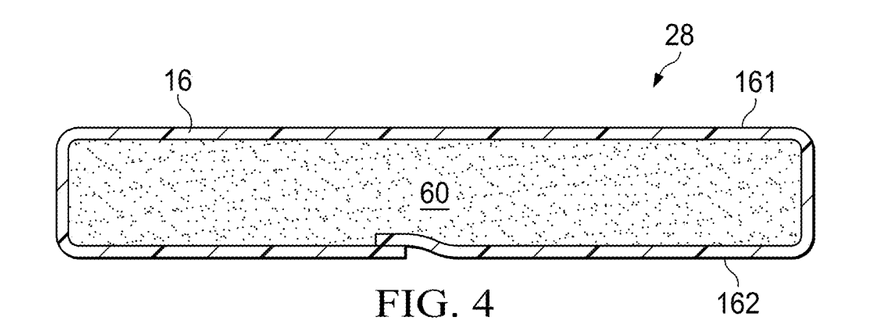
FIG. 4 is a partial sectional view along 2-2 of another alternative embodiment of the absorbent core of absorbent article of FIG. 1.
Figure 5:
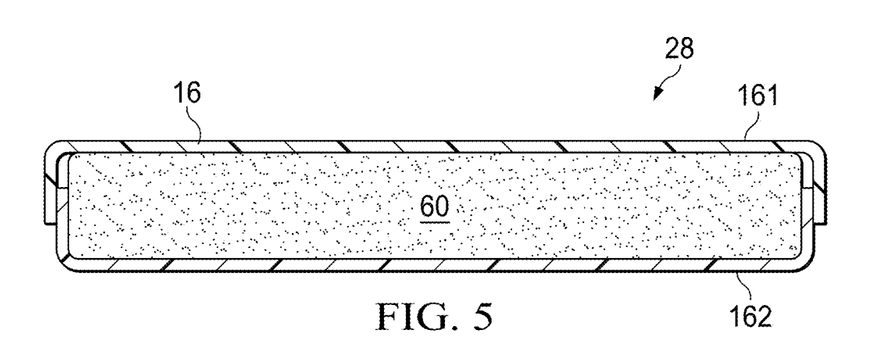
FIG. 5 is a partial sectional view along 2-2 of another alternative embodiment of the absorbent core of absorbent article of FIG. 1.
Figure 6:
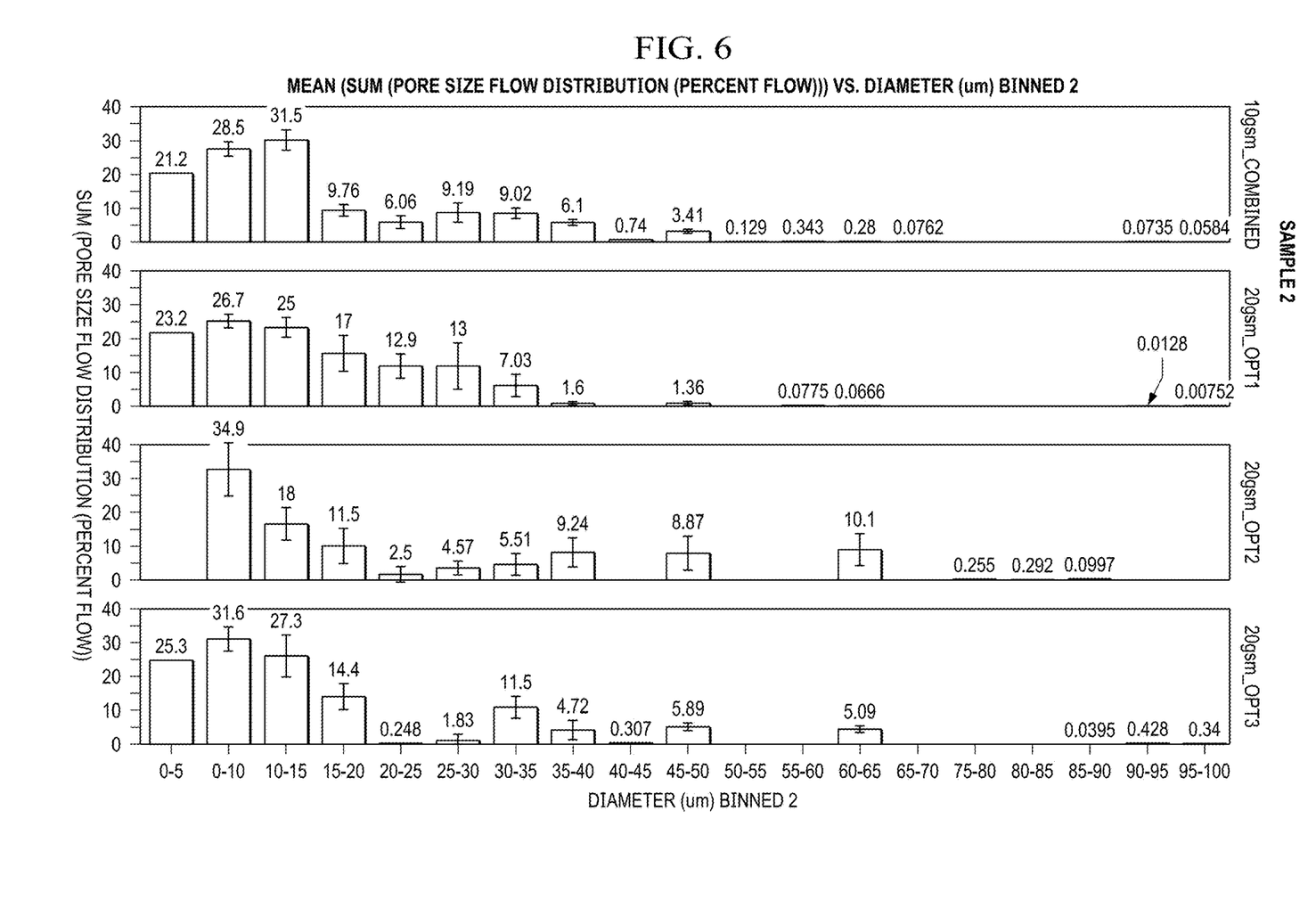
FIG. 6 graphically illustrates the pore size distribution of nonwoven samples A, B, C and D with respect to Example 2.

In FIG. 3, the absorbent material 60 is wrapped by a core wrap 16 in a C-fold. In FIG. 4, the absorbent material 60 is surrounded by the core wrap 16, and the edges of the core wrap 16 are sealed together to enclose the absorbent material 60. In FIG. 5, the absorbent material 60 is surrounded or enveloped by two nonwoven webs, a fluid receiving top layer 161 and a bottom layer 162.

In some embodiments, a core wrap comprises a nonwoven web of the present application. In such embodiments, at least a bottom layer of a core wrap comprises a nonwoven web of the present application.

Backsheet

The backsheet may be positioned such that it includes at least a portion of the garment-facing surface of the absorbent article. The backsheet may be designed to prevent the exudates absorbed by and contained within the absorbent article from soiling articles that may contact the absorbent article, such as bed sheets and undergarments. The backsheet may be substantially water-impermeable. Suitable backsheet materials may include breathable materials that permit vapors to escape from the absorbent article while still preventing exudates from passing through the backsheet 26. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. Suitable materials and/or manufacturing techniques may be used to provide a suitable backsheet including, but not limited to, surface treatments, particular film selections and processing, particular filament selections and processing, etc. The backsheet may also include more than one layer configured, for example, as discrete, unjoined layers or as laminate comprising a film layer and a nonwoven layer. It is to be appreciated that such laminate structures are not limited to the backsheet, but may be incorporated into any of the absorbent article components described herein or commonly known in the art (e.g., ears or sides panels), as desired. When the backsheet comprises a laminate a film layer and a nonwoven layer, in some embodiments, the film layer forms a wearer-facing side of the backsheet. The elastomeric film layer may be formed from a styrenic block copolymer or an elastomeric polyolefin (e.g., VISTAMAXX brand elastomeric polypropylene resin available from Exxon Chemical Company), and the nonwoven layer may include mono-component and/or multi-component fibers.

The backsheet may comprise a wetness indicator.

Wetness Indicator

A wetness indicator in the absorbent article according to the present invention comprises a wetness indicator composition. It is disposed on and/or in a substrate constituting a component of an absorbent article so that it is located between an absorbent core and a backsheet. The substrate may include, but is not limited to, woven fabrics, nonwoven fabrics, films, sponges, and combinations thereof. The wetness indicator composition may be applied on any layer of the absorbent article using a conventional technique, for example printing, spraying or coating, or printed adhesive coating as indicated previously, during the making of the absorbent article. This allows the wetness indicator to be visible from the exterior of the article by transparency through the backsheet while keeping the wetness indicator composition within the article.

The wetness indicator maybe applied to a substrate via any means of liquid or semi-liquid application as known in the art, including, but not limited to, slot coating, spraying, gravure printing, ink jet printing, and digital printing. Alternatively, the wetness indicator may be a solid or semi-solid material affixed to a substrate via adhesive bonding, chemical bonding or intermolecular force bonding. Multiple indicators may be applied to the same substrate in overlapping or nonoverlapping geometries.

It may be desirable that the wetness indicator is present in more adjacent substrates (e.g., a bottom layer of a core wrap disposed on the garment-facing side of the absorbent core) in addition to the substrate to which it has been applied (e.g., backsheet) to ensure desirable wicking of fluid (e.g., urine) to the wetness indicator composition after the occurrence of a wetness event. That is, when a gap exists between the wetness indicator and an adjacent substrate such as a bottom layer of a core wrap, fluid may not travel from the absorbent core to the wetness indicator within the desired time to signal the occurrence of a wetness event. Thus, it may be desirable to apply the wetness indicator composition at a suitable predetermined temperature such that effective coating of both the backsheet and the bottom layer of a core wrap occurs without bleeding of the composition to regions within the diaper, which may undesirably impact the colorant's stability.

It may additionally be desired that there is substantial contact/adherence/liquid communication to the adjacent substrate to ensure that the wetness indicator composition is evenly (top to bottom and side to side) wetted and thus provides the full signal intended.

Wetness indicators suitable for use with the lower basis weight and/or breathable films and nonwovens described above include compositions of straight chain alkyl moieties (which are correlated with the open time of the wetness indicator) having a chain length from about C12 to about C300, from about C14 to about C100, or from about C16 to about C50. Further, the wetness indicators herein may be applied at a basis weight of greater than about 10 $g/m^2$, greater than about 20 $g/m^2$, or greater about 25 $g/m^2$, but typically less than 100 $g/m^2$. Furthermore, suitable wetness indicators that include a phosphate free acid may have a phosphorous content of 10.0% or less, of 1.0% or less, or of 0.1% or less.

In one exemplary embodiment, the wetness indicator may initially be applied as a molten composition to an inner face (i.e., the wearer-facing side) of the backsheet of an absorbent article such that it adheres to the backsheet. Then, the outer face (i.e., the garment-facing side) of the bottom layer of a core wrap of an absorbent article may be brought into contact with the wetness indicator such that the wetness indicator contacts/adheres to the bottom layer of a core wrap over the entire (or substantially entire) surface of the wetness indicator. In this example, the wetness indicator is in liquid communication with the absorbent core (i.e., the bottom layer of a core wrap is disposed between the backsheet and core), and therefore can provide a wetness event signal visible from outside the substrate when the product is being worn (i.e., visible to a wearer, a caregiver, parent and the like).

The wetness indicator compositions maybe present on a substrate in any desired pattern or configuration. The wetness indicating compositions may be applied in any pattern or in conjunction with permanent graphics, such as, permanent graphics on the outer surfaces of a disposable absorbent article or component thereof.

In certain embodiments, the wetness indicator, when present on a substrate, may be applied at levels that are effective at providing visible signals, and it is to be understood that the amount of wetness indicator present on a substrate will depend upon many factors such as, but not limited to, substrate type (e.g., thick, thin, opacity, bulky, dense, other physical properties), substrate material, intended use of the substrate (e.g., disposable diaper, panty liner, bandage), method used for applying the wetness indicator compositions, desired intensity of signal in either dry or after contacting liquid, desired kinetics for the color change, desired stability of the color within the wetness indicator composition, desired pattern or configuration of the wetness indicator composition on substrate, and combinations thereof.

Nonwoven Web

A nonwoven web of the present invention suitable for an absorbent article comprises a first layer comprising filament fibers, a second layer comprising filament fibers, and a third layer comprising staple fibers disposed between the first and second layers.

In some embodiments, a nonwoven web of the present invention suitable for an absorbent article comprises a first layer comprising spunbond nonwoven, a second layer comprising spunbond nonwoven, and a third layer comprising meltblown nonwoven disposed between the first and second layers. In such embodiments, the nonwoven may be comprise spunbond-meltblown-spunbond (SMS) nonwoven.

The nonwoven web of the present invention has a unique pore size distribution. In the nonwoven web, greater than about 80%, or greater than 85%, or greater than 90%, or greater than 95% of the pores has a pore size equal to or smaller than about 40 µm. In the nonwoven web, less than about 10%, or less than 5%, or less than 3% of the pores has a pore size equal to or greater than about 45 µm. In some embodiment, the nonwoven web has less than 10% of pores having a pore size equal to or greater than 35 µm.

In the nonwoven of the present invention, a total basis weight of the first and second layers is not less than about 10 gsm, or not less than 14 gsm, or not less than 18 gsm in order to meaningfully mask a grainy feel due to SAP particles in an absorbent core. In some embodiments, the second layer has a basis weight lower than the first layer. The second layer may have a basis weight lower than 10 gsm, or lower than 8 gsm. An increased basis weight may affect a wetness indicator trigger time.

The third layer has a basis weight no greater than about 4 gsm or no greater than 3 gsm, or no greater than 2 gsm. If a basis weight of the third layer is too high, the color change time of the wetness indicator during the wetness event may be significantly delayed.

The nonwoven web may have a basis weight in the range of about 12 gsm-about 50 gsm, or about 15 gsm-about 40 gsm, or about 20 gsm-about 30 gsm.

The nonwoven web may have an air permeability in the range of about 60 to about 300 $m^3/m^2/min$, or about 60 to about 200 $m^3/m^2/min$, or about 101 to about 300 $m^3/m^2/min$.

Without intending to be bound by any particular theory, it is believed that the unique pore size distribution and having a second layer in a limited basis weight in the nonwoven web of the present invention may allow a wetness indicator composition penetrates through the nonwoven web in a broader area on a surface and/or deeper depth in z-direction in the nonwoven web. When the nonwoven web of the present invention is incorporated in an absorbent article comprising a wetness indicator, in some embodiments, in the making process of the absorbent article, the wetness indicator may be heated to be a liquid form and printed on a back sheet, for example on a wearer-facing side of the backsheet, and contact the nonwoven web sometimes also with pressures. Nonwoven web with smaller pore sizes normally may provide a higher capillary force to suck the liquid wetness indicator, and more surface for wetness indicator to stay within the nonwoven web. The pressure applied during the absorbent article making process may also help to transfer the wetness indicator towards the nonwoven web. The wetness indicator may be transferred to on the nonwoven web having smaller pores. When the wetness indicator is transferred to broader and/or deeper on to the nonwoven web, the color change time of the wetness indicator is shorter during the wetness event. Therefore, it is desirable to have as a narrow pore size distribution and a small percentages of pores having a high pore size illustrated above to fast a wetness indicator trigger time.

The nonwoven web of the present invention may have a mean pore size equal to or smaller than 45 µm, or equal to or smaller than 39 µm, or equal to or smaller than 35 µm, or equal to or smaller than 30 µm. Without intending to be bound by any particular theory, having a smaller mean pore size may be especially important when the basis weight of the nonwoven web increases, as otherwise the wetness indicator trigger time will increase significantly.

The nonwoven web may be formed by direct extrusion processes during which the fibers and the nonwoven materials are formed at about the same point in time, or by preformed fibers which can be laid into nonwoven materials at a distinctly subsequent point in time.

One or more individual layers can be created by each process. For instance, SMS can mean a three layer, 'sms' nonwoven materials, a five layer 'ssmms' nonwoven materials, or any reasonable variation thereof wherein the lower case letters designate individual layers and the upper case letters designate the compilation of similar, adjacent layers.

The fibers in nonwoven webs are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof.

A nonwoven web of the present invention and fibers constituting the nonwoven web can be subjected to additional treatment after formation. For nonwoven webs, additional treatment commonly occurs after the fibers are joined to one another (post-treatment). Examples of additional treatments include but are not limited to mechanical stresses, chemical additives, or combinations thereof.

A nonwoven web of the present invention when it is SMS nonwoven may be made by any conventional methods for producing SMS nonwoven known in the art. For example, the nonwoven can be produced via a spunbond process that can be combined with the meltblown process a layered laminate.

A spunbonding process comprises supplying a molten polymer, which is then extruded under pressure through a large number of orifices in a plate known as a spinneret or die. The resulting continuous fibers are quenched and drawn by any of a number of methods, such as slot draw systems, attenuator guns, or Godet rolls, for example. In the spunbonding process, the continuous fibers are collected as a loose web upon a moving foraminous surface, such as a wire mesh conveyor belt, for example. When more than one spinneret is used in line for forming a multi-layered web, the subsequent nonwoven component layers are collected upon the uppermost surface of the previously formed nonwoven component layer.

The meltblowing process is for forming a layer of a nonwoven material, wherein, a molten polymer is extruded under pressure through orifices in a spinneret or a die. High velocity gas impinges upon and attenuates the fibers as they exit the die. The energy of this step is such that the formed fibers are greatly reduced in diameter and are fractured so that micro-fibers of indeterminate length are produced. Although the laydown of meltblown fibers and their orientation is considered as a random process, the laydown might be adjusted by the air temperature, die temperature, air flow settings of cooling air, die-collector distance, belt vacuum and quenching temperature and time.

Meltblown nonwoven structures by a meltblown process are added to a first spunbond nonwoven structures produced by a spunbond process, and a second spunbond nonwoven structures produced by a spunbond process to form a SMS web.

After laying down the number of S- and M-layer required the nonwoven may be consolidated using known techniques, typically thermal point bonding. In thermal point bonding, heat is applied locally on individual regions of the nonwoven to locally melt and fuse the fibers together.

The present invention is also directed to absorbent article comprising a nonwoven web according to the present invention and a wetness indicator. The absorbent article of the present invention has a wearer-facing side and a garment-facing, and comprises a liquid pervious topsheet, a liquid impervious backsheet, an absorbent core disposed between the topsheet and the backsheet, the absorbent core comprising an absorbent material and a core wrap, a nonwoven web of the present invention, and a wetness indicator.

In certain embodiments, the absorbent article of the present invention has the nonwoven web of the present invention disposed between the absorbent core and the backsheet.

In certain embodiments, the absorbent article of the present invention comprises a core wrap comprising the nonwoven web of the present invention. In the embodiments, at least a bottom layer of the core wrap comprises a nonwoven web of the present invention.

In some embodiment, an absorbent article of the present invention comprises a liquid pervious topsheet, a liquid impervious backsheet, an absorbent core comprising an absorbent material and a core wrap comprising a nonwoven web, and a wetness indicator between the absorbent core and the backsheet. In such embodiment, the backsheet may comprise a wetness indicator. In such embodiments where the wetness indicator is in direct contact with the outer face (i.e., garment-facing side) of a bottom layer of the core wrap, the bottom layer of a core wrap has a wetness indicator stain area where a wetness indicator composition adhere or transferred, and has about more than 20%, or more than 25%, or more than 30% of a % wetness indicator stain area when measured according to the Wetness Indicator Stain Area described below under MEASUREMENT. When a % wetness indicator stain area is lower than 20%, the color change time of the wetness indicator during the wetness event may be significantly delayed.

The absorbent article of the present invention may comprise an absorbent core comprising about 80%, about 85%, about 90% or about 95% of superabsorbent polymer particles by weight of the absorbent material.

The absorbent article provides improved softness feel by masking a grainy feeling.

Absorbent Article Manufacturing Process

The absorbent articles of the invention may be made by any conventional methods known in the art. In particular the articles may be hand-made or industrially produced at high speed. Typically, adjacent layers and components will be joined together using conventional bonding method such as adhesive coating via slot coating or spraying on the whole or part of the surface of the layer, or thermo-bonding, or pressure bonding or combinations thereof. Other glues or attachments are not represented for clarity and readability but typical bonding between the layers of the article should be considered to be present unless specifically excluded. Adhesives may be typically used to improve the adhesion of the different layers, for example between the backsheet and the core wrap. The glues used may be any standard hotmelt glue as known in the art.

In one embodiment, a process for producing an absorbent article of the present invention comprises: a) supplying a topsheet material having a wearer-facing surface and a garment-facing side, b) supplying an absorbent core to the garment-facing side of a topsheet material, the absorbent core having a wearer-facing surface and a garment-facing side, and c) supplying a backsheet material to the garment-facing side of the absorbent core, the backsheet material comprising a wetness indicator, wherein the absorbent core comprises an absorbent material and a core wrap at least partially covering the absorbent material, the core wrap comprising a nonwoven web of the present invention.

Measurement

Air Permeability

Using a TexTest Instruments Air Permeability Tester FX 3300 LABOTESTER III (available from TexTest Instruments, Schwerzenbach, Switzerland) or equivalent, measure the air permeability of the samples according to EDANA 140.1-99 with the following settings.

Samples are conditioned 24 hours and measured at 23° C., 50% relative humidity for at least 2 hours.

Using a circular test area of 20 cm$^2$ and a pressure drop of $Ap=200$ Pa. Avoid areas in a sample that has been folded, creased or otherwise physically damaged.

Report results in m$^3$/(m$^2$·min) as the arithmetic mean of 5 single measurements taken on different samples.

Pore Size

The pore size distribution of a nonwoven web is measured by the capillary flow porometer, Porolux 100, from Porotec (DE) or equivalent.

When a nonwoven web is a component such as a core wrap of an absorbent article a pre-treatment needs to remove adhesive and an absorbent material, etc. A nonwoven web isolated from an absorbent articles is rinsed with cool water while gently rubbing with fingers to remove any adhered absorbent material such as absorbent materials from the nonwoven web. When removal of adhesive form the nonwoven web is desired, the nonwoven web is submerged in an appropriate solvent (such as tetrahydrofuran) to remove glue for approximately 10 minutes at ambient temperature before being allowed to dry.

The measured area for each specimen is a circle with 4.5 mm diameter. A nonwoven web sample is cut, and placed into the sample chamber of the instrument and the chamber is then sealed. The highest pressure of the blowing air is set at 0.1 bar. The dry nonwoven web sample is firstly measured as the base for the air flow, in the unit of L/min. The air pressure keeps increasing and air flow is measured after it passing through the dry nonwoven web, and the test stops when the air flow hits the highest pressure as set up. The air flow versus pressure data represents the "dry curve." Then, the nonwoven web sample is fully soaked in a low surface tension fluid with a surface tension liquid of 15 mN/m, namely Galwick with a surface tension of 15.9 mN/m. The soaked nonwoven web sample is placed into the sample chamber of the instrument and the chamber is then sealed. Upon starting the automatic measurement cycle, air flows into the sample chamber behind the nonwoven web sample and then the air pressure is slowly increased via the computer to a value sufficient to overcome the capillary action of the fluid in the pore having the largest diameter in the nonwoven web sample. The air flow versus pressure data represents the "wet curve." With the delta between the dry air flow curve and the wet air flow curve, the computer calculates the pore parameters including the mean pore size and a histogram of pore diameters across the tested range (e.g., from the bubble point down to about 0.08 microns or even less with higher air pressure) as is known to those of skill in the porous media field.

Wetness Indicator Trigger Time

The wetness indicator trigger time is measured by loading the absorbent article with 0.9% saline solutions on the skin facing side. The absorbent article is present with a camera placed underneath so that it can video tape the wetness indicator during and after the loading process. The wetness indicator trigger time is counted between the start of the loading process, and the start of the wetness indicator color change.

Wetness Indicator Stain Area

Sample Preparation

An absorbent article is sufficiently wetted by loading 150 g of 0.9% saline on a wearer-facing side of the absorbent article at the full length of a wetness indicator. After waiting for a few minutes and a color of the wetness indicator is fully changed, a backsheet is carefully separated from the absorbent article to expose a garment-facing surface of a core wrap of an absorbent core. An area of the wetness indicator stain on the garment-facing surface of the core wrap is measured.

Image Acquisition

An image of a garment-facing surface of the absorbent core having where wetness indicator stain is observed is taken using a lab-built image acquisition system. The key components include a Canon camera (Canon EOS 6D Mark 2) with lens (EF 24-105 mm f/4L IS 2 USM), a dome light (Smart Vision Lights DLP-600*600-WHI) and a non-reflective black background plate, or equivalent of each of the components. The absorbent core with wetness indicator mounted on a plastic plate is placed at the center of the black background plate. The camera is mounted right above the absorbent core with a distance of 105 mm. The dome light is mounted under the camera with a distance of around 50 mm.

The camera settings used for the image acquisition are: Focal length: 85 mm; ISO: 100; Aperture: F8.0; Exposure time: $1/125$ s. These settings enable the image to have a proper exposure and contrast, and may be adjusted to ensure a proper exposure and contrast.

Image Analysis

The image analysis of the wetness indicator stain area on an absorbent core (core wrap) is conducted by the following steps:

i. The acquired image is firstly imported into the Image J software (version. 1.52 h, National Institute of Health, USA, or equivalent). Then, a rectangle area is selected to crop out the Wetness indicator stain area. The width of the rectangle is around 25 mm; the length of the rectangle is around 200 mm. The rectangle size can be adjusted to capture an entire wetness indicator stain area.

ii. The cropped images are separated to three channels: Hue, Saturation, Brightness by using the "HSB" stack module. The "Saturation" channel is used to do the Wetness indicator stain area calculation.

iii. The "Saturation" channel image is firstly binarized by using Otsu thresholding method, which results into a binary image with pixel gray level of wetness indicator set to 255 and the rest set to 0. Then the total number of pixels that has a gray level of 255 is summed together. Finally, the area of wetness indicator is obtained by multiply the total count with the physical area of a single pixel.

Wetness indicator stain area=Pixel Count(wetness indicator)*Area(single pixel)

% Wetness indicator stain area=(wetness indicator stain area/original wetness indicator)*100

EXAMPLES

Example 1: Nonwoven and Diaper Preparation

Various samples of nonwoven web A-D specified in Table 1 below were manufactured. In all nonwoven web A-D, spunbond nonwoven and meltblown nonwoven were produced polypropylene polymers.

TABLE 1

| Sample No. | A | B | C | D |
|---|---|---|---|---|
| Material Type | sms | ssms | ssms | ssms |
| Total Basis Weight (g/m$^2$) | 10 | 20 | 20 | 20 |
| Basis weight of layers (g/m$^2$) | 4/2/4 | 6/6/2/6 | 6/6/2/6 | 6/6/2/6 |

Samples of taped diapers A-D were manufactured using Pampers Hajimeteno Hadaeno Ichiban (Procter and Gamble Japan K.K. Japan) by replacing a bottom layer of a core wrap with Nonwovens A-D, respectively. Pampers Hajimeteno Hadaeno Ichiban has a wetness indicator printed on a backsheet film in the area of 4 mm width, and 190 mm length at the particular "S" size of the Taped Diaper. (SJ: Is this description correct? Or, is Diaper A Hichiban itself, and diapers B-D were prepared according to the description?) YY: Yes it's correct. Only watch out that the WI length varies by size of the diaper. Therefore I think using % is better than absolute WI stain area.

Example 2: Nonwoven Properties

Various properties of samples of nonwoven web manufactured in Example 1 were tested and are displayed in Table 2. Nonwoven B is an embodiments of nonwoven web materials of the present disclosure, while nonwovens A, C and D are provided merely for comparison purposes.

TABLE 2

|  | Nonwoven A | Nonwoven B | Nonwoven C | Nonwoven D |
|---|---|---|---|---|
| Air Permeability m³/(m² · min) | 225.6 | 129.4 | 196.1 | 211.5 |
| Mean Pore size | 39.9 | 26.7 | 65.8 | 67.0 |

Pore size distribution of the Nonwoven webs A-D from Example 1 were measured according to the Pore Size Measurement described in the MEASUREMENT section above.

Figure 7A:
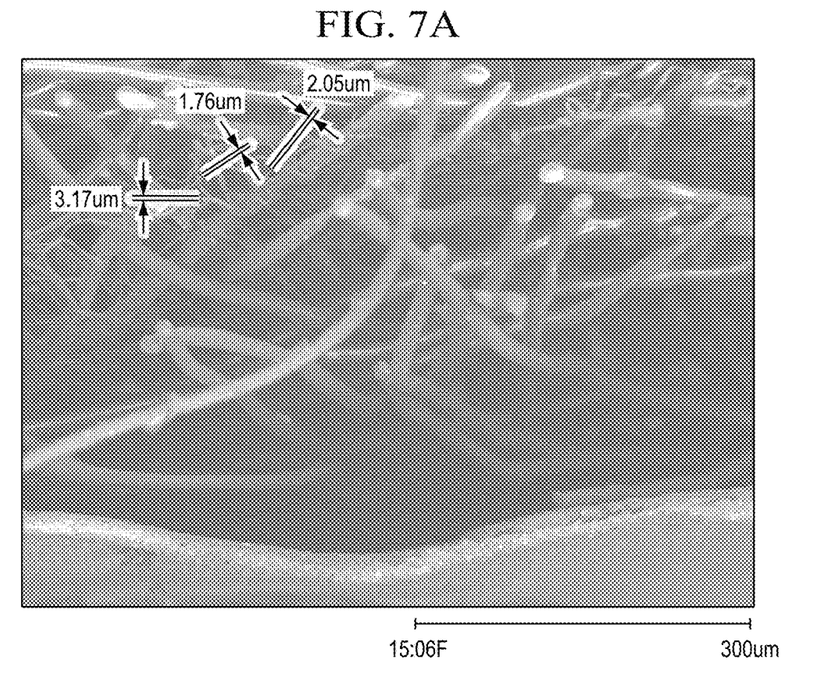
FIG. 7A is a scanning electron microscope image of a cross section of a nonwoven web according to the present invention.
Figure 7B:
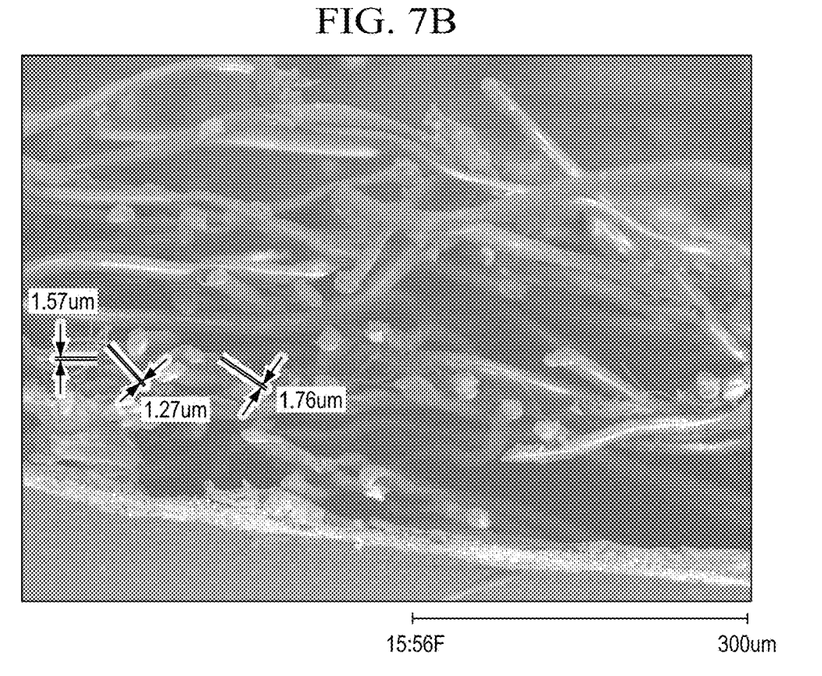
FIG. 7B is a scanning electron microscope image of a cross section of a nonwoven web.

FIGS. 7A and 7B are SEM (TM3000, Hitachi) images of cross sections of nonwoven B and D. The diameter of fibers in the nonwoven was determined by using a Scanning Electron Microscope (SEM) and image analysis software. A magnification of 250 was chosen such that the fibers were suitably enlarged. Nonwoven B has a smaller dimeter of meltblown layer fibers than nonwoven D.

Example 3: Grainy Feel Sensory and Wetness Indicator Trigger Time

Diaper A-D manufactured in Example 1 were tested for grainy feel sensory as below, and for and wetness indicator trigger time according to the Wetness Indicator Trigger Time described in the MEASUREMENT section above. Results are displayed in Table 3.

8 trained sensory panelists were provided with diapers A-D and 2 control diapers, one was with very grainy feeling ("grainy sample") and the other one was without grainy feeling at all ("no grainy sample"). Panelists touched each diaper to feel grainy feeling of the diaper and provided a score between 1 to 10 points describing how they felt about the grainy feeling of each absorbent article with reference to the grainy sample assigned point 1 and the no grainy feel assigned point 10. The average score of scores from all the panelists is the final sensory score of the tested samples.

TABLE 3

|  | Diaper A | Diaper B | Diaper C | Diaper D |
|---|---|---|---|---|
| Wetness indicator trigger time (sec) | 20.5 | 29.8 | 47.4 | 48.8 |
| Sensory, grainy feel | 5.6 | 6.5 | 6.5 | 6.6 |

1 point difference: noticeable difference
2 point difference: significant difference

Example 4: Wetness Indicator Stain Areas

Wetness indicator stain areas in core wraps in diaper A-D prepared in Example 1 were measured and % Wetness indicator stain areas were calculated according to the method described in the Wetness Indicator Stain Area in the MEASUREMENT section above. Results are displayed in Table 4.

TABLE 4

|  | Diaper A | Diaper B | Diaper C | Diaper D |
|---|---|---|---|---|
| Wetness indicator stain area (mm²) | 405 | 257 | 76 | 105 |
| % Wetness indicator stain area* | 53.4% | 33.8% | 10.0% | 13.8% |

*Original wetness indicator stain area: 760 mm²

The dimensions and values disclosed herein are not to be understood as being strictly limited to the exact numerical values recited. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web for an absorbent article, the nonwoven web comprising a first nonwoven layer comprising filament fibers, a second nonwoven layer comprising filament fibers, and a third nonwoven layer comprising staple fibers disposed between the first and second nonwoven layers;
    wherein a total basis weight of the first and second nonwoven layers is not less than about 10 gsm;
    wherein the third nonwoven layer has a basis weight no greater than about 4 gsm;
    wherein the nonwoven web comprises pores; and
    wherein a first plurality of the pores have a pore size between 10 μm and 15 μm, and wherein a second plurality of the pores have a pore size equal to or greater than 45 μm.

2. The nonwoven web of claim 1, wherein the nonwoven web comprises a spunbond-meltblown-spunbond web.

3. The nonwoven web of claim 2, wherein the nonwoven web has an air permeability in the range of about 60 m³/m²/min to about 300 m³/m²/min.

4. The nonwoven web of claim 1, wherein the nonwoven web has a mean pore size equal to or smaller than about 45 μm.

5. An absorbent article having a wearer-facing surface and a garment-facing surface, the absorbent article comprising:
- a liquid pervious topsheet;
- a liquid impervious backsheet; and
- an absorbent core disposed between the topsheet and the backsheet, the absorbent core comprising an absorbent material and a core wrap comprising a nonwoven web; and
- a wetness indicator between the absorbent core and the backsheet;
- wherein the nonwoven web comprises a first nonwoven layer comprising filament fibers, a second nonwoven layer comprising filament fibers, and a third nonwoven layer comprising staple fibers disposed between the first and second nonwoven layers;
- wherein a total basis weight of the first and second nonwoven layers is not less than about 10 gsm;
- wherein the third nonwoven layer has a basis weight no greater than about 4 gsm;
- wherein the nonwoven web comprises pores;
- wherein greater than about 80% of the pores have a pore size equal to or smaller than about 40 μm;
- wherein less than about 10% of the pores have a pore size equal to or greater than about 45 μm; and
- wherein the nonwoven web has a mean pore size equal to or smaller than 30 μm.

6. The absorbent article of claim 5, wherein the nonwoven web comprises a spunbond-meltblown-spunbond web.

7. The absorbent article of claim 5, wherein the absorbent material comprises at least about 80% of superabsorbent polymer particles, by weight of the absorbent material.

8. The absorbent article of claim 5, wherein the second nonwoven layer of the nonwoven web faces the backsheet and has a basis weight lower than a basis weight of the first nonwoven layer.

9. The absorbent article of claim 5, wherein the second nonwoven layer has a basis weight less than about 10 gsm.

10. The absorbent article of claim 5, wherein the nonwoven web has about 20% or more of a wetness indicator stain area, when measured according to the Wetness Indicator Stain Area.

* * * * *